(12) United States Patent
Samadpour

(10) Patent No.: US 10,246,669 B2
(45) Date of Patent: *Apr. 2, 2019

(54) METHOD FOR PRODUCING HYPOALLERGENIC PEANUT PRODUCTS

(71) Applicant: Molecular Epidemiology Inc., Lake Forest Park, WA (US)

(72) Inventor: Mansour Samadpour, Lake Forest Park, WA (US)

(73) Assignee: Molecular Epidemiology Inc., Lake Forest Park, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,409

(22) Filed: Mar. 14, 2018

(65) Prior Publication Data

US 2018/0201881 A1    Jul. 19, 2018

Related U.S. Application Data

(60) Continuation of application No. 14/687,809, filed on Apr. 15, 2015, now Pat. No. 9,932,545, which is a division of application No. 13/776,145, filed on Feb. 25, 2013, now Pat. No. 9,856,438.

(51) Int. Cl.
| | |
|---|---|
| *C11D 3/386* | (2006.01) |
| *A23L 5/20* | (2016.01) |
| *A23L 11/30* | (2016.01) |
| *A23L 25/00* | (2016.01) |

(52) U.S. Cl.
CPC ............ *C11D 3/38618* (2013.01); *A23L 5/25* (2016.08); *A23L 11/33* (2016.08); *A23L 25/00* (2016.08); *A23V 2002/00* (2013.01); *C12Y 304/22033* (2013.01)

(58) Field of Classification Search
None
See application file for complete search history.

(56) References Cited

U.S. PATENT DOCUMENTS

| 3,317,325 A | 5/1967 | Durst |
| 5,266,473 A | 11/1993 | Nielsen |
| 8,211,485 B2 | 7/2012 | Ahmedna |
| 2008/0305211 A1 | 12/2008 | Ahmedna |
| 2010/0080870 A1 | 4/2010 | Ahmedna |

OTHER PUBLICATIONS

Astwood, J.D., et al., "Stability of Food Allergens to Digestion in vitro," National Biotechnology 14:1269-1273, 1996.
Beuchat, L.R., et al., "Physiochemical Properties of Peanut Flour as Affected by Proteolysis," Journal of Agricultural and Food Chemistry 23(4):616-620, Jul. 1975.
Brenda, "Brenda: Information on EC 3.4.22.32—Stem Bromelain," <http://brenda-enzymes.org/enzyme.php?ecno=3.4.22.32> [ retrieved Apr. 11, 2016], 20 pages.
Chemicalbook, "Bromelain From Pineapple Stem 2 u/mg," <http://www.chemicalbook.com/ChemicalProductProperty_EN_CB7497142.htm> [retrieved Dec. 22, 2014], 2 pages.
Downing, D.L., "A Complete Course in Canning and Related Processes, Book III, Processing Procedures for Canned Food Products" 14th ed., CTI Publications, Inc., Baltimore, Maryland, 2015, Chapter 12, "Packing Dry or Reduced-Water-Activity Products," pp. 385-392.
Eiwegger, T., et al., "Gastro-Duodenal Digestion Products of the Major Peanut Allergen Ara h 1 Retain an Allergenic Potential," Clinical & Experimental Food Allergy 36(10):1281-1288, 2006.
Hu, C.-Q., et al., "Changes of Peanut Allergens During Processing," 27(12):784-788, Shipin Kexue (Beijing, China), 2006.
Jackson, L.S., et al., "Cleaning and Other Control and Validation Strategies to Prevent Allergen Cross-Contact in Food Processing Operations," Journal of Food Protection 71(2): 445-458, Feb. 2008.
Koppelman, S.J., et al., "Digestion of Peanut Allergens Ara h 1, Ara h 2, Ara h 3, and Ara h 6: A Comparative in vitro Study and Partial Characterization of Digestion-Resistant Peptides," Journal of Molecular Nutrition and Food Research 54:1711-1721, 2010.
Kornblum, Z.C., and C. Union, "Water," Encyclopedia Americana, <http://edelsteincenter.files.wordpress.com/2010/07/water.pdf> [retrieved Dec. 22, 2014], 7 pages.
Maleki, S.J., et al., "The Effects of Roasting on the Allergenic Properties of Peanut Proteins," Journal of Allergy and Clinical Immunology 106(4):763-768, Oct. 2000.
Tanabe, S., et al., "Modification of Wheat Flour With Bromelain and Baking Hypoallergenic Bread With Added Ingredients," Bioscience, Biotechnology, and Biochemistry 60(8):1269-1272, 1996.
Wako Pure Chemical, "Active Pharmaceutical Ingredients Catalog," <http://wako-chem.co.jp/english/labchem/journals/ActivePharmaceuticalIngredients/index2.html#9-2.-Other-Anti-Inflammatory-Agents> [retrieved Dec. 22, 2014], 52 pages.
Yu, J., et al., "Enzymatic Treatment of Peanut Kernals to Reduce Allergen Levels," Food Chemistry 127:1014-1022, 2011.

*Primary Examiner* — Thomas J. Visone
*Assistant Examiner* — Evelyn Y Pyla
(74) *Attorney, Agent, or Firm* — Barry L. Davison; Davis Wright Tremaine LLP

(57) ABSTRACT

A peanut food product with reduced levels of allergenic proteins such as Ala h1/h2/h3 is produced by initiating the germination process in raw peanuts, holding the peanuts in moist conditions to initiate germination, and then treating with bromelain.

17 Claims, 2 Drawing Sheets

METHOD FOR PRODUCING HYPOALLERGENIC PEANUT PRODUCTS

CROSS REFERENCE TO RELATED APPLICATION

This application is a continuation of U.S. patent application Ser. No. 14/687,809, filed Apr. 15, 2015, which is a divisional of U.S. patent application Ser. No. 13/776,145, filed Feb. 25, 2013, now U.S. Pat. No. 9,856,438, the disclosures of which are hereby incorporated by reference herein in their entirety.

SUMMARY OF THE INVENTION

Provided are peanut food products with reduced levels of major allergenic proteins including Ara h1, Ara h2, and Ara h3 is produced by soaking raw or roasted, shelled peanuts in a solution containing bromelain. The resulting product may be further processed to create edible peanut products. Also provided is a process for treating (e.g., spraying with a bromelain solution such that particles of peanut are rendered non-allergenic) tiny particles of peanuts which adhere to machinery in food-processing plants, to provide for enhanced safety of the machinery with respect to allergens when it is subsequently used for other products that are expected to be free from peanut allergens.

DESCRIPTION OF THE INVENTION

Figure 1:
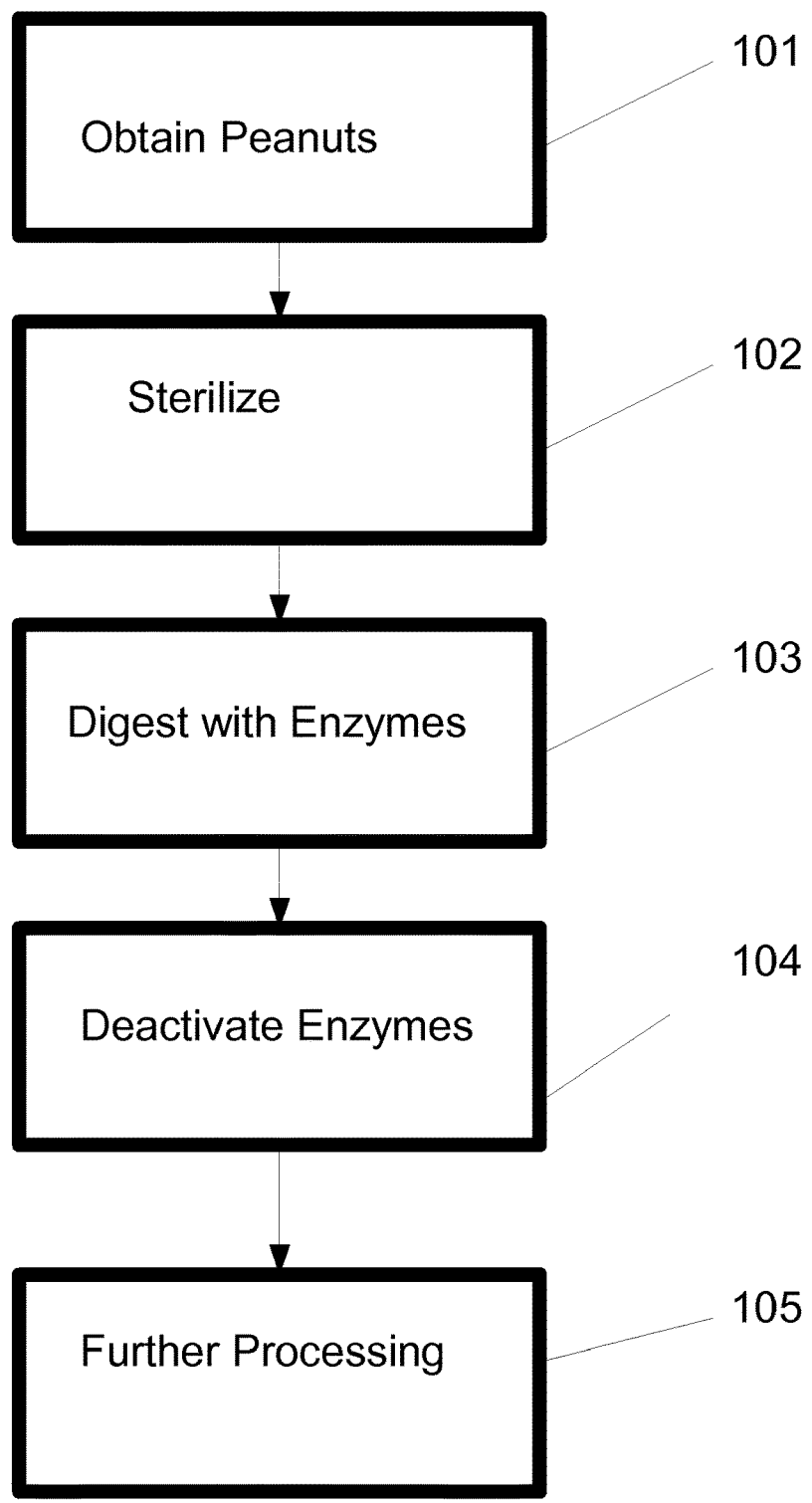
FIG. 1 is a flow chart showing steps of the inventive method.

Peanuts contain certain proteins, termed allergens, which can cause allergic reactions in some people. Some of these proteins, specifically Ara h1, Ara h2, and Ara h3, are associated with allergic reactions. For purposes of this application, such proteins are collectively referred to as allergenic proteins. It has been discovered that allergenic proteins in peanuts may be reduced or eliminated by the method disclosed herein such that an ultimate peanut product is rendered hypoallergenic. The method comprises the step of soaking raw or roasted, shelled peanuts in a solution containing stem bromelain. It has been found that soaking for a period of four hours in a concentration of 10 g per liter (1% w/v) bromelain is effective.

Bromelain is a crude extract, derived from members of the Bromeliacene family, that is used in the food industry as a meat tenderizer on account of its aggressive proteolytic activity. The stem (waste) portion of the pineapple is the customary source of bromelain, and typically, this encompasses the enzyme stem bromelain, together with the enzymes comosain and ananain.

After bromelain treatment, the peanuts are preferably heated to inactivate the enzyme. Then the peanuts are preferably dried to remove excess moisture absorbed during the enzyme treatment step. The result is a non-allergenic peanut that may be released into commerce for use in any application in which standard peanuts might be used.

Raw peanuts processed with this method may subsequently be roasted. A suitable time and temperature for this roasting has been found to be 60 minutes in a home-style, non-convection oven at a temperature of 350 F.

Finally, the peanuts may be subjected to assays for determining the presence of allergenic proteins to verify that the resulting product is, indeed, hypoallergenic.

Preferably shelled peanuts are sanitized prior to soaking by exposure to bleach solution, which acts to prevent microbial growth during the enzyme treatment step. The peanuts are rinsed after this step to remove the bleach.

The present invention affords a method for producing non-allergenic, non-ground whole, half, and broken peanuts pieces that have the culinary and usability characteristics of nuts, as opposed to nut flour. A discussion of the physical difference in the structure of nuts and nut pieces versus flour is set forth in U.S. Pat. No. 3,317,325, issued to Durst (hereinafter "Durst") (Cols. 1 and 2), and is incorporated by reference herein. As there described, a peanut cotyledon, which is the largest part of the edible nut, comprises a continuous phase of carbohydrate, protein, fiber and ash and a discontinuous phase of fat, with fat cells in the form of lakes that are surrounded by non-fat constituents. As used in the description, the term peanut piece is a portion of cotyledon that retains the continuous carbohydrate-protein phase, and also the fat lakes, as in the raw, unprocessed peanut. Further (Durst, Col. 1, line 58), it is defined that grinding of the cotyledons results in a paste wherein the fat forms a continuous phase and the non-fat particles are discontinuous from each other, such that there is no longer a continuous phase of carbohydrate, protein, etc. (Durst, Col. 1, lines 57-65.)

An unground or non-ground peanut is here defined to be a nut or nut piece that has not been subjected to grinding, such that the non-fat particles maintain their original connectedness. In the discussion herein, the term "intact fat cells" refers to those lakes, i.e., contiguous areas of fat that are to be found in a peanut prior to grinding.

DISCUSSION OF PRIOR ART

The present invention provides non-allergenic, non-ground peanuts and peanut pieces that retain intact fat cells in the form found in the raw peanut and also the continuous phase of carbohydrate, protein, fiber, and ash surrounding these fat cells, as in the raw peanut. The result is a product which retains a nut-like identity and culinary characteristics, as opposed to being a mere flour or paste. This distinguishes the present invention from the art disclosed in U.S. Pat. No. 5,266,473, issued to Nielsen (hereinafter "Nielsen") which pertains only to peanut flour.

The present invention provides greatly improved results over previous methods, such as that disclosed in U.S. patent application Ser. No. 11/758,823, by Ahmedna (hereinafter "Ahmedna '823"), and in U.S. patent application Ser. No. 12/631,325, by Ahmedna (hereinafter "Ahmedna '325"). Our review of these applications and our testing of Ahmedna's proposed method shows that allergens are not, in fact, eliminated to the same extent as the method proposed herein. This is because the enzymes proposed for use by Ahmedna, trypsin, pepsin, and alpha-chymotrypsin, do not attenuate the major allergen proteins Ara h1, Ara h2, and Ara h3 in unground nuts as well as does the method disclosed herein.

Data presented in Ahmedna '823 was obtained from samples that were ground to powder, dissolved into a solution, and then centrifuged. Then, only the supernatant portion was tested, with the centrifugation pellet, apparently, being ignored. (See Ahmedna '823 at paragraphs [0131] and [0046]). The same procedure, ignoring the insoluble fraction represented by the centrifugation pellet, was also followed in Ahmedna '325 (paragraphs [0045], [0061], and [0077]). In a recent paper, the authors of these applications conceded that trypsin and alpha-chymotrypsin do not operate to reduce Ara h 1 and Ara h2 significantly in raw peanuts. J. Yu, Ahmedna, et al., *Food Chemistry* 127 (2011), page 1018, paragraph 3.3. FIG. 5 of the same paper shows a strong band for Ara h2 remaining after enzyme treatment of roasted peanuts. Thus, use of trypsin and alpha-chymotrypsin does not result in hypoallergenic peanuts, whether the treatment be upon raw or roasted nuts.

One reason for the failure of Ahmedna to actually remove the allergens is suggested by Eiwegger, et al., 36 *Clinical and Experimental Food Allergy* 1281-1288(2006), who assessed the ability of pepsin, trypsin, and alpha-chymotrypsin to degrade purified Ara h1 obtained from defatted peanut meal. Eiwegger made the finding that while the discrete Ara h1 band is efficiently digested, peptide fragments of <10 kD are generated that remain antigenically intact as per western blot analysis, and moreover, that pepsin-mediated digested peptides remained fully immunologically active as per the ability to stimulate peanut-specific T and B cell proliferation. This finding is supported by data published by Maleki, et al., *J Allergy Clin. Immunol.* 106: 763-768 (2000), who show that 5-8 IgE binding fragments of Ara h1 can be detected in the range of 16-60 kDa following treatment with pepsin, trypsin, and alpha-chymotrypsin. Thus from Maleki et al., and Eiwegger et al., it is evident that treatment of Ara h1 with these enzymes does not eliminate the immunological aspects. Furthermore, analyses of Ara h2 digestion using crude pepsin, trypsin, or alpha-chymotrypsin enzyme preparations conclude that this protein is resistant to the activity of these enzymes, Astwood, et al., *Nat. Biotech.* 14:1269-1273 (1996); Koppelman, et al., 54 *Journal of Molecular Nutrition and Food Research* 1711-1721 (2010).

DETAILED DESCRIPTION OF INVENTION

It has been discovered that the key to removing allergens is to avoid use of the enzymes proposed in Ahmedna (U.S. patent application Ser. No. 11/758,823 (hereinafter "Ahmedna '823") and Ser. No. 12/631,325 (hereinafter "Ahmedna '325")), and to use bromelain instead. Moreover, it has been found that fruit bromelain will not work adequately. Rather, stem bromelain from the leaves and stem of the pineapple is required. In the provided examples herein, "bromelain" refers to "stem bromelain" unless otherwise noted.

FIG. 1 is a flow chart showing the steps of the inventive method. Peanuts, step 101, are obtained as a starting product. Input peanuts may be raw, or they may be roasted, or in some processed form such as peanut butter or flour. The inventive method is particularly attractive for use with raw peanuts since it is uniquely able to deal with allergens contained in an intact peanut matrix.

The incoming product is sanitized 102. This step is not strictly required.

However, it provides assurance that microorganisms will not grow in the product during the subsequent steps of the process. Sanitization may be accomplished by soaking a 15% bleach solution for 15 minutes or so.

The sanitized product is digested 103 with a protease enzyme, preferably stem bromelain, obtained from the vegetative portions of the pineapple plant or other members of the Bromeliaceae family. After digestion for a suitable period of time, the enzymes are preferably deactivated 104, using heat or some other method. The product is then ready for further processing 105. If raw peanuts were the input product, these may proceed to roasting if desired.

Figure 2:
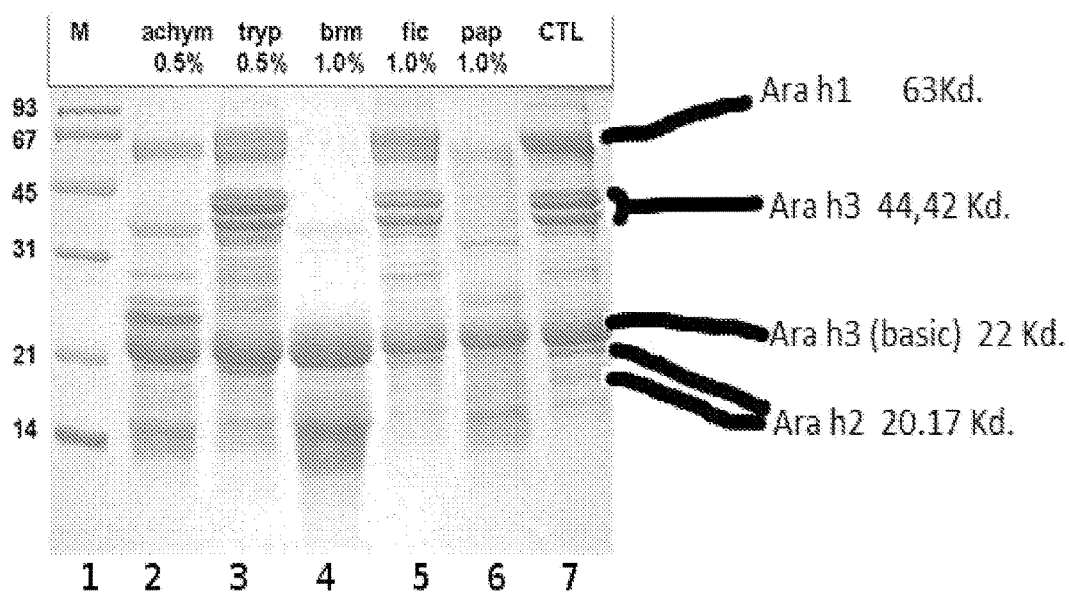
FIG. 2, PLATE A, is a photograph of an SDS-PAGE gel comparing effectiveness of various enzymes in reducing peanut allergens. PLATE B is a photograph of a Western Blot prepared with mixed serum from peanut-sensitive patients.
Figure 2:
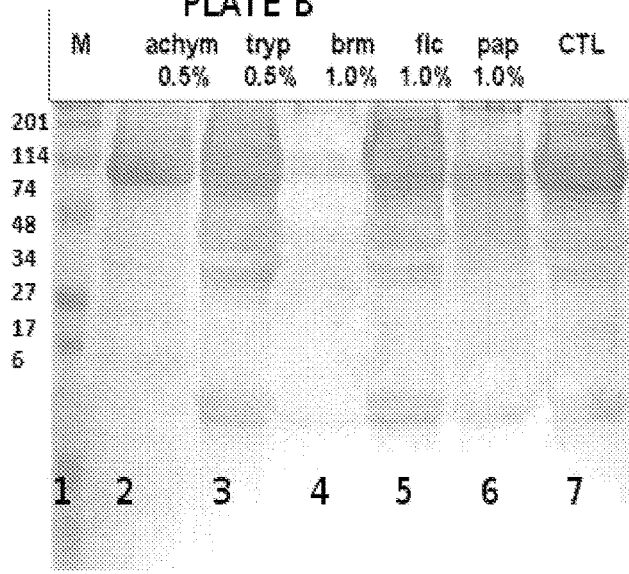

FIG. 2, PLATE A, is a gel photograph showing bands pertaining to the Ara h1, h2, and h3 allergens. Lanes 1-7 indicated on PLATE A are as follows: (1) Molecular Weight ladder for calibration; (2) extract from peanuts treated with alpha-chymotrypsin; (3) extract from peanuts treated with trypsin; (4) extract from peanuts treated with stem bromelain; (5) extract from peanuts treated with ficin; (6) extract from peanuts treated with papain; and (7) untreated peanut as a control. The attenuation of bands in bromelain-treated peanuts as compared to other enzymes indicates that allergens have been greatly reduced. It is clear from the optical density of the bands that Ara h1 63Kd. and Ara h3 44, 42 Kd. have been virtually eliminated, to an extent greater than 90%, as have been the Ara h2 bands at 20 and 17Kd. The Ara h3(basic) band at 22 Kd persists, but this band is not thought to represent an allergen for most otherwise sensitive people.

FIG. 2, PLATE B, is a western blot of the same samples, against a mixed serum obtained from multiple adult and child peanut-sensitive people. This serum was obtained from Bioreclamation, LLC under product number HMSRM-PEANUT. Lane 4, pertaining to Bromelain, indicates that allergenicity has been virtually eliminated from these raw peanut samples.

Since different strains and varieties of peanuts may have mutations in the genes for Ara h1, Ara h2, and Ara h3 and other allergens, various mutant forms of allergenic protein may theoretically exist from variety to variety. That is why it is important to verify the end result of the inventive process with allergen assays. The exact variety and source of peanuts for input into this inventive process is a results-effective variable ultimately determined by the final assays.

The product of these processing steps may be used in the normal manner as a food product to be used as any other peanut product, for example as a food topping, material for peanut butter production, subsequent roasting, etc.

It is believed that allergenic proteins other than Ara h1/h2/h3 will be degraded in a similar manner by the process described herein. The experimental focus was upon Ara h1/h2/h3 because these are the three allergens that are associated with severe allergic reactions such as anaphylaxis. However, it is expected that other, lesser allergenic components such as Ara h4/h5/h6/h7/h8 may be similarly influenced by this process. This is confirmed by the western blot against a generalized mixed peanut serum shown in Plate B of FIG. 2.

A particular application of this process involves treating tiny particles of peanuts which adhere to machinery in food-processing plants. Machinery may be sprayed with a bromelain solution such that particles of peanut are rendered non-allergenic. This will promote safety of the machinery with respect to allergens when it is subsequently used for other products that are expected to be free from peanut allergens.

The method of the present invention provides a way of treating peanut kernels or parts thereof to render the peanut material hypoallergenic or non-allergenic. In the method of this invention, the peanut, or parts thereof, is contacted with an aqueous solution of bromelain under temperature, pH, and time parameters that are optimal for the enzyme to penetrate the nut and function therein. The nut is encapsulated by the epidermis and surrounding cuticle, punctuated by stomata. The matrix is structurally complex, being composed of parenchymal cells and vascular networks that envelop starch grains, protein (aleurone) bodies, and lipid spherosomes. The storage proteins in peanut kernels are largely restricted to the aleuron bodies, membrane-bound storage organelles. Thus the optimized conditions detailed herein reflect the needs to circumvent the hindrances imposed on by the nut itself as well as the inherent ability of the enzyme to degrade the peanut allergens.

According to the invention, peanut kernels are contacted with an aqueous solution bromelain. If desired, the peanut can first be sanitized prior to the treatment with bromelain, to assist in reducing the microbial content. Sanitization might consist of treatment of the nut with a solution of 10% Chlorox bleach for 30 minutes followed by sufficient rinsing with water to remove the sanitizing agent.

The effective pH range of bromelain is 4.0 to 9.0 with the optimal dependent upon the substrate being treated. For peanuts, the desired pH is 5.0. In instances where this approach is applied to the treatment of other allergenic foods, the pH might require additional adjustment. The pH at which bromelain optimally digests other allergenic foods can be readily determined by one having ordinary skills in the art of measuring enzymatic activity of a protease over a range of pH values. The pH of the aqueous solution may be adjusted by the additions of buffers, acids, bases, or salts in a conventional manner to obtain the desired pH of the aqueous solution. The preferred buffer in this invention is a combination of 0.05% citric acid (w/v), 0.005% ascorbic acid (w/v) adjusted with NaOH to pH 5.0. Citric acid and ascorbic acid are used widely in the food industry as food preservatives/conservatives and have the added benefit of exerting antioxidant effects.

The effective concentration of bromelain needed to digest allergenic proteins depends on the food being treated. For peanuts, the desired concentration is 0.5% to 1.0% bromelain or 5 g-10 g/L buffer. This value is equivalent to 700,000-1,650,000 casein digesting units (CDU)/ml of buffer. Enzyme may be added in amounts above or below this preferred range. However, addition of substantially lower amounts can increase the duration of the reaction time, while greater amounts of enzyme would be a needless expense. The concentration of bromelain needed to digest allergens contained in other foods would depend on the precise nature of the food being treated. The concentration at which bromelain optimally digests other allergenic foods can be readily determined by one having ordinary skills in the art of measuring enzymatic activity of a protease.

The buffer containing dissolved enzyme is added to the peanuts in an amount sufficient to hydrate and deliver the enzyme effectively. In a preferred embodiment, the ratio of nut to added buffer volume is 1:1, where 1 g of nut is contacted with 1 ml of solution. Solution may be added in amounts above or below this value. The desired ratio at which bromelain optimally digests other allergenic foods can be readily determined by one having ordinary skills in the art of measuring enzymatic activity of a protease.

The effective temperature range of bromelain is 35° C.-65° C. with the optimum being 50° C.-60° C. In a preferred embodiment, the temperature is maintained at 37° C. In another aspect of the embodiment, the temperature is 52° C. While a 37° C. condition is more economical, digestion at 52° C. has the benefit of expediting the rate of proteolysis as well as serving to curb microbial growth over the treatment period.

The duration of the enzyme treatment needed to enable effective removal of the allergens from the peanut may be monitored by sampling aliquots of peanuts to determine the optimal reaction time for a particular reaction vessel, temperature, concentration, and peanut format.

Allergenicity can be monitored by extracting the proteins and performing SD S-PAGE analysis at different time points. Reaction times of 30 minutes to 4 hours are generally sufficient to adequately reduce the allergen content. In a preferred embodiment, the time for bromelain activity is 4 hours at 37° C. However, periods of time, either longer or shorter, may be applied depending on the precise reaction conditions being employed.

The type of reaction vessel used for treating the peanut with bromelain is not critical, though preferably the vessel should incorporate an aspect that enables gentle agitation during treatment. In a preferred embodiment, agitation can be obtained using a rotary device operating at roughly 10-30 rpm on a horizontal axis. Additional embodiments would include a rotary device that operates on a vertical plain or a silo-mixer vessel. In each embodiment, the mixing device preferably should maintain the optimal reaction temperature over the course of the reaction time.

After the enzyme reaction has been completed, the nuts are rinsed of the enzyme solution and then dried to reduce the moisture content of the nut and to inactivate the enzyme. Suitable drying means are well known in the art and include heating at 90° C. for 16 minutes or heating at 70° C. overnight. Alternatively, the nuts may then be subject to roasting process, which can include heating at 170° C. for 16 minutes.

The allergenicity of the treated nut can be determined by methods known in the art. As noted above, specific proteins in the peanut that are capable of causing allergic reactions are known as allergens. The immunoreactivity of the treated nut can be determined by extracting the peptide fragments generated by proteolysis, subjecting them to SD S-PAGE and western blot analysis so as to assess the scope of cleavage and the ability of the cleavage fragments to bind human immunoglobulin, IgG or IgE isotypes, derived from peanut allergic subjects. Additional analyses that can employed include ELISA, probing for IgG or IgE derived from peanut allergic sera, as well as cell-based assays that can report on the ability of the fragmented allergen to crosslink IgE on the surface of a cell.

Peanut or peanut derivatives manufactured according to the methods outlined herein have retained full nutritional composition and organoleptic properties and can thus be utilized to prepare conventional dietary and food compositions containing peanuts according to known recipes and using known methods. In addition, the method can be extended to the treatment of manufacturing equipment to remove allergenic residues contaminating the surfaces. Finally, application of this method can be extended to reducing the allergenic content of other food stuffs, particularly those with complex food matrices.

In another embodiment of this invention, whole peanuts are soaked prior to being subjected to digestion enzymes. The soaking is for a sufficient time and at appropriate temperatures to permit the seeds to germinate. Germination of the peanut opens up the seed matrix and permits enzymes to penetrate, and additionally generates enzymes from the peanut itself, which assists the added bromelain in breaking down allergen proteins. Optionally, germination alone may be used to reduce allergen proteins.

The inventive method is applicable to other legumes and tree nuts having allergenic storage proteins.

What is claimed is:

1. A method of decontaminating machinery contaminated with allergen residues, comprising: contacting machinery contaminated with seeds of legumes, peanuts or tree nuts, or unground pieces or particles thereof, having Ara h3 allergen with an aqueous solution of bromelain in an amount and for a time period sufficient to reduce or eliminate the allergenicity of the Ara h3 allergen.

2. The method of claim 1, wherein the Ara h3 allergen is embedded in peanuts, or in unground pieces or particles thereof.

3. The method of claim 2, wherein the peanuts, or the unground pieces or particles thereof are raw, blanched, or roasted.

4. The method of claim 2, wherein contacting the machinery contaminated with the peanuts, or the unground pieces or particles thereof with the aqueous solution of bromelain, comprises: moving the aqueous solution of bromelain relative to the peanuts, or to the unground pieces or particles thereof; moving the peanuts, or the unground pieces or particles thereof relative to the aqueous solution of bromelain; or both.

5. The method of claim 2, wherein the bromelain comprises stem bromelain derived from any plant member belonging to the family Bromeliaceae.

6. The method of claim 2, wherein contacting the machinery contaminated with the peanuts, or the unground pieces or particles thereof with an aqueous solution of bromelain is at a pH in the range of 2 to 10.

7. The method of claim 6, wherein contacting the machinery contaminated with the peanuts, or the unground pieces or particles thereof with an aqueous solution of bromelain is at a pH in the range of 4 to 6.

8. The method of claim 2, wherein the aqueous solution of bromelain comprises bromelain in an amount in a range selected from the group consisting of: 0.1% to 2% bromelain (wt/vol); and of 0.5% to 1% bromelain (wt/vol).

9. The method of claim 2, further comprising at least one of: sanitizing or sterilizing the peanuts, or the unground pieces or particles thereof prior to contacting with the aqueous solution of bromelain; and/or inactivating the bromelain during or after the contacting with the aqueous solution of bromelain.

10. The method of claim 9, wherein sanitizing or sterilizing the peanuts, or the unground pieces or particles thereof comprises treating, spraying or soaking the peanuts, or the unground pieces or particles thereof in an aqueous solution comprising a sanitizing or sterilizing agent; and washing the treated, sprayed or the soaked peanuts, or the unground pieces or particles thereof to remove the sanitizing or sterilizing agent.

11. The method of claim 9, wherein the sanitizing or sterilizing agent comprises an oxidizing agent.

12. The method of claim 9, wherein inactivating the bromelain comprises at least one of heat inactivation of the bromelain after contacting with the aqueous solution of bromelain; and/or autodigestion of the bromelain during contacting with the aqueous solution of bromelain.

13. The method of claim 1, wherein the allergenicity of the Ara h3 allergen is reduced by at least 90% by the bromelain-mediated digestion.

14. The method of claim 1, further comprising, prior to contacting the machinery contaminated with the peanuts, or the unground pieces or particles thereof with an aqueous solution of bromelain, holding the peanuts, or the unground pieces or particles thereof for a period of time under conditions of moisture and temperature sufficient to initiate germination.

15. The method of claim 1, wherein the bromelain comprises stem bromelain derived from any plant member belonging to the family Bromeliaceae.

16. The method of claim 1, wherein contacting the machinery contaminated with the seeds of legumes, peanuts or tree nuts, or unground pieces or particles thereof with an aqueous solution of bromelain is at a pH in the range of 2 to 10.

17. The method of claim 1, wherein the aqueous solution of bromelain comprises bromelain in an amount in a range selected from the group consisting of: 0.1% to 2% bromelain (wt/vol); and of 0.5% to 1% bromelain (wt/vol).

* * * * *